(12) United States Patent
Nagasawa et al.

(10) Patent No.: US 6,897,021 B2
(45) Date of Patent: May 24, 2005

(54) REACTIVE PROBE CHIP, COMPOSITE SUBSTRATE AND METHOD FOR FABRICATION OF THE SAME

(75) Inventors: Hiroshi Nagasawa, Osaka (JP); Akira Fukunaga, Kanagawa-ken (JP); Masayoshi Hirose, Kanagawa-ken (JP)

(73) Assignee: Ebara Corporation, Tokyo (JP)

( * ) Notice: Subject to any disclaimer, the term of this patent is extended or adjusted under 35 U.S.C. 154(b) by 204 days.

(21) Appl. No.: 09/820,778

(22) Filed: Mar. 30, 2001

(65) Prior Publication Data

US 2001/0039072 A1 Nov. 8, 2001

(30) Foreign Application Priority Data

Mar. 30, 2000 (JP) ........................................ 2000-094529
Sep. 27, 2000 (JP) ........................................ 2000-294462
Sep. 27, 2000 (JP) ........................................ 2000-294463

(51) Int. Cl.$^7$ ........................ C12Q 1/68; G01N 33/53; C07H 21/04
(52) U.S. Cl. ........................ 435/6; 435/7.1; 536/22.1; 536/23.1
(58) Field of Search ........................ 435/6, 7.1, 91.1, 435/91.2; 536/22.1, 23.1, 24.3, 24.33

(56) References Cited

U.S. PATENT DOCUMENTS

| | | | |
|---|---|---|---|
| 4,803,154 A | | 2/1989 | Uo et al. |
| 5,436,327 A | | 7/1995 | Southern et al. |
| 5,514,550 A | * | 5/1996 | Findlay et al. ................. 435/6 |
| 5,703,223 A | * | 12/1997 | Wickstrom et al. ...... 536/25.33 |
| 5,830,767 A | | 11/1998 | Bauman et al. |
| 5,843,767 A | * | 12/1998 | Beattie .................... 435/287.1 |
| 5,968,728 A | | 10/1999 | Perttunen et al. |
| 6,207,369 B1 | | 3/2001 | Wohlstadter et al. |
| 6,238,909 B1 | * | 5/2001 | Choong et al. .......... 435/287.2 |
| 6,288,220 B1 | | 9/2001 | Kambara et al. |
| 6,569,674 B1 | * | 5/2003 | McGarry et al. ........ 435/287.2 |

FOREIGN PATENT DOCUMENTS

| | | |
|---|---|---|
| EP | 0 468 585 A2 | 1/1992 |
| EP | 0 895 083 A2 | 7/1998 |
| JP | 09178753 | 11/1997 |
| JP | 112211727 | 6/1999 |
| JP | 2001183378 | 6/2001 |
| WO | WO 00/33078 | 6/2000 |

* cited by examiner

*Primary Examiner*—Kenneth R. Horlick
*Assistant Examiner*—Joyce Tung
(74) *Attorney, Agent, or Firm*—Browdy and Neimark, P.L.L.C.

(57) ABSTRACT

A reaction probe chip which is prepared by loading a reactive probe on fine pieces of carrier such as particles, tile-like plates and then arraying and immobilizing the reactive probe-loaded carrier on a base material. The carrier fine pieces such as particles, tile-like plates and the like are porous or have a reactive surface, and the base material is preferably a thin inorganic plate or a thin organic plate is disclosed.

The inorganic base material is preferably a glass slide or silicon wafer, and the organic base material is preferably a polyester film or polyethylene film. In case the porous carrier pieces are used, the reactivity of the inner surfaces of the porous carrier pores should be maintained during array or immobilization process of the reactive probe-loaded carrier.

A composite substrate characterized in that on at least a section of the surface thereof, a plurality of porous regions are orderly arranged as compartments by non-porous regions, or a plurality of non-porous regions are orderly arranged as compartments by porous regions is also disclosed. The porous solid is preferably porous glass or porous ceramic, the porous glass is preferably split-phase porous glass, and the surface is preferably flattened by a process such as polishing.

62 Claims, 8 Drawing Sheets

REACTIVE PROBE CHIP, COMPOSITE SUBSTRATE AND METHOD FOR FABRICATION OF THE SAME

BACKGROUND OF THE INVENTION

The present invention relates to a reactive probe chip capable of recognizing a plurality of functional molecules, to be used for gene diagnosis, physiological function diagnosis and the like, and to a method for its fabrication.

Also, the present invention relates to a composite substrate wherein on at least a section of the surface thereof, a plurality of porous regions are arrayed as compartments encompassed by non-porous regions, or a plurality of non-porous regions are arrayed as compartments encompassed by porous regions, and to a method for its fabrication.

Detection of polymorphisms due to gene mutations, and particularly single base (codon) mutations, is not only effective for diagnosis of cancer and other diseases resulting from mutations, but is also necessary for indication of drug responsiveness and side-effects, and can be helpful for the analysis of the causative genes of multiple factor diseases, and for predictive medicine. The use of "DNA chips" for detection is known to be effective. The hitherto utilized "Gene Chip" by Affymetrix, which is a DNA chip containing immobilized short DNA chains, usually comprises over 10,000 oligo DNA fragments (DNA probes) mounted on an approximately 1 cm square silicon or glass plate using a photolithographic technique.

When a fluorescently-labeled DNA sample to be examined is allowed to flow over the DNA chip, the DNA fragments having sequences complementary to the probes of the DNA chip bind to the probes to perform detection of only those sections by their fluorescence, and thereby detecting and quantifying the specific sequences of DNA fragments in the DNA sample. It has already been demonstrated that this method can detect cancer gene mutations and gene polymorphisms.

Microarrays with cDNA immobilized on slide glass may also be used.

On the other hand, porous solids have been widely used in the prior art as carriers for catalysts, enzymes, microorganisms and the like, and are utilized as sites for various reactions. They are also used as functional materials for adsorption and separation, or as materials providing low heat or electrical conductivity. Porous glass or porous ceramics are used as porous solids, and methods of controlling the pore sizes or imparting functional groups have provided properties suitable for specific uses.

There were three principal problems in the prior art. DNA chips employing photolithography require at minimum four photomasks for each step of synthesis, and the photolithography, coupling and washing must be repeated four times. Since this is repeated the required times depending on the chain length, the cost is high (problem 1). Also, it is necessary to change each photomask in order to change the pattern, for which reason, DNA chips with various designs could not be flexibilly fabricated (problem 2).

That is, although the types of DNA probes to be immobilized on the DNA chip are previously decided and although it is easy to fabricate and supply such DNA chips at locations where the necessary equipment is available, different photomasks must be prepared for synthesis of each base in the probe. Therefore, the reaction process has may steps and it is difficult to fabricate in a flexible manner, DNA chips containing DNA probes for different purposes. High costs are also incurred. When the number of DNA probes required is small, the degree of integration of the DNA probes on the chip need not be so high. Rather, it is sometimes desirable for the chip to have the desired DNA probes immobilized in a more convenient manner. The DNA chip must also be provided at low cost and with high stability if it is clinically used to detect DNA polymorphisms of individuals.

Alternatively DNA Microarray chips prepared by spotting a solution of synthesized oligonucleotide at high density, is proposed. In this process, modifying groups are introduced after synthesis of the oligonucleotides and then the modified oligonucleotides are cut out and released from the carrier and purified. Further the purified oligonucleotides are reacted with the functional groups previously introduced onto the substrate glass. Thus, the process is very complex and the cost is therefore high (problem 3) as of the DNA chips produced by photolithography.

Which respect to substrates for probe chips, porous solids have a wide variety of applications, for example, carrier of probe chips such as DNA chips, and the like, but the use of porous solids having continuous porous regions throughout the entire surface has been limited in that only one function can be loaded on such a single and uniform substrate.

However, in recent advancements in scientific techniques, downsized devices is in ever greater demand and it has been desired to develop a composite substrate having unique utilities not found in the prior art, and a substrate having different reaction sites with a plurality of functions on the single substrate whereby the local areas of the substrate can be thermally or electrically insulated each other.

In light of the problems in the prior art, it is an object of the present invention to provide a composite substrate as a single substrate allowing a plurality of different functions to be loaded, as well as a method for its fabrication.

SUMMARY OF THE INVENTION

The present invention solves the aforementioned problems with respect to reactive probe chips and to composite substrates by way of the following means.

According to one aspect of the invention, porous carrier particles are used as a carrier fine pieces to be loaded with reactive substances or reactive probes.

(1) A reactive detecting chip characterized in that fine porous carrier particles having reactive substances, which have ability to bond different detection targets and which are loaded on the inner surfaces of the porous particle pores, serve as a whole porous carrier particle probes. They are arrayed and bound or immobilized on at least one of a plurality of microcompartments provided on a base material, while maintaining the reactivity of the inner surfaces of the porous carrier particle pores.

(2) A reactive probe chip according to (1) above, wherein the porous carrier particles loaded with the reactive probes are of a material having a bonding surface, such as porous glass, silica gel or ion-exchange resin.

(3) A reactive probe chip according to (1) or (2) above, wherein the pore size of the porous carrier particles ranges from 10 nm to 1 µm, and the particle size is from 1 µm to 100 µm.

(4) A reactive probe chip according to any one of (1) to (3) above, wherein the base material immobilizing the porous carrier particles loaded with the reactive is an inorganic base material or organic base material.

(5) A reactive probe chip according to any one of (1) to (4) above, wherein the reactive probes to be loaded in the porous carrier particles are DNA, RNA or PNA (peptide nucleic acid) or fragments thereof, oligonucleotides of any desired base sequence, antigens, antibodies or epitopes, or enzymes, proteins or their partial polypeptide chains having the target functions.

(6) A method for fabrication of a loaded porous carrier particles wherein a solid phase method is used to synthesize oligonucleotides having desired base sequences or proteins having desired structures on porous carrier particles, and they are used as they are.

(7) A method for fabrication of a loaded porous carrier particles, which comprises binding DNA, RNA or PNA (peptide nucleic acid) or fragments thereof, oligonucleotides of any desired base sequences, antigens, antibodies or epitopes, or enzymes, proteins or polypeptide chains which are a part of the proteins and have the functions, to porous carrier particles using a binding material.

(8) A method for fabrication of a reactive probe chip, characterized in that the one or more loaded porous carrier fine particles fabricated according to (5) or (6) above are arrayed and bound or immobilized in at least one of a plurality of microcompartments provided on a base material while maintaining the reactivity of the inner surfaces of the porous carrier particle pores.

According to one aspect of the invention, oligonucleotides having any desired base sequence or proteins having any desired structure may be synthesized on porous carrier particles with a surface of the binding ability, such as porous glass, silica gel or ion-exchange resin, by a solid phase method. Alteratively, the reactive substances or probes such as DNA, RNA or PNA (peptide nucleic acid) or fragments thereof, oligonucleotides of any desired base sequences, antigens, antibodies or epitopes, or enzymes, proteins or their fragments staining their functions, are bound to the porous carrier particles using some sort of binding material. Thus, the loaded porous carrier particle probes are produced.

The produced particulate probes may be used alone or in combination, and bound or immobilized utilizing a dispenser or printing method, on at least one of a plurality of microcompartments provided on a base material. The base material is selected from an inorganic base material such as a slide glass or silicon wafer or an organic base material such as a polyester film or polyethylene film. The probes are bound on the base material while maintaining the reactivity of the inner surfaces of the porous carrier particle pores.

For the binding and immobilization of the porous carrier particles in an orderly fashion on the base material according to the invention, only the outer surfaces of the carrier particles are used for immobilization, and a protective measure such as impregnation with water is utilized in order to accomplish immobilization without incurring damage to the inner pore surfaces by an adhesive component used for the immobilization.

In accordance with another aspect of the invention, the aforementioned problems can be solved by arraying and binding reactive substances or probes on tile-like carriers, and then arranging and immobilizing each tile-like carrier on a base material.

Another aspect of the present invention solves the aforementioned problems by way of the following means.

(1) A reactive probe chip characterized in that tile-like carriers loaded with reactive substances are arrayed and immobilized on a base material.

(2) A reactive probe chip according to (1) above, wherein the tile-like carriers loaded with the reactive substances are of a material having a reactive surface, and then the base material immobilizing the carriers includes a thin inorganic or organic plate.

(3) A method for fabrication of a reactive probe chip, characterized in that enzymes, antigens, DNA fragments, antibodies, epitopes or proteins are arrayed and immobilized on tile-like carriers, and each of the loaded carriers is immobilized in an orderly fashion in separate compartments on the base material.

(4) A method for fabrication of a reactive probe chip according to (3) above, wherein after synthesizing oligonucleotides with desired base sequences on tile-like carriers, each carrier is immobilized in an orderly fashion into separate compartments on the base material.

(5) A method for fabrication of a reactive probe chip according to (3) or (4) above, wherein the tile-like carriers are each a plate with a square shape having a size of from 50 $\mu$m to 5 mm on each side, or a hexagonal or circular shape, and they are mechanically attached and immobilized on the base material.

In still another aspect of the present invention, an excellent composite substrate which, can exhibit a plurality of different functions as a single substrate, is provided.

The aspect of the present invention has been completed by focusing attention on applicability not found in the prior art and by providing a composite substrate wherein either a plurality of porous regions are arrayed and comparted by non-porous regions, or a plurality of non-porous regions are arrayed and comparted by porous regions on at least a section of the surface of a porous solid conventionally used in the form of particles. The composite substrate provides reaction sites with a plurality of different functions on the same substrate, or to thermally or electrically insulate specific regions of the substrate.

Still another aspect of the present invention solves the aforementioned problems by way of the following means.

(1) A composite substrate characterized in that on at least a section of the surface thereof, a plurality of porous regions are arrayed on a substrate material and comparted by non-porous regions, or a plurality of non-porous regions are arrayed and comparted by porous regions.

(2) A composite substrate according to (1) above, wherein a composite substrate comprising both porous regions and non-porous regions has a surface flattened by, for example, a polishing process.

(3) A method for fabrication of a composite substrate, wherein the composite substrate according to (1) above is produced by situating a separately formed porous solid at predetermined regions on a non-porous substrate.

(4) A method for fabrication of a composite substrate according to (3) above, characterized in that the formation of the composite substrate is accomplished by situating a plurality of porous solid precursors at predetermined regions on a non-porous substrate and producing pores in the porous solid precursors placed on the substrate.

(5) A method for fabrication of a composite substrate according to (3) above, wherein formation of the plurality of porous regions is accomplished by producing pores in a plurality of predetermined porous solid precursor regions on a substrate the entire surface of which is a porous solid precursor.

DETAILED DESCRIPTION OF THE INVENTION

It is a characteristic of one aspect of the present invention that the oligonucleotides constituting the DNA probes are bound on the inner pore surfaces of the porous carrier particles, so that the porous carrier particles act as "loaded porous carrier particulate probes" as they are.

Another aspect of the present invention is directed to a reactive probe chip characterized in that a plurality of particulate or tile-like carriers loaded with reactive probes are immobilized in separate compartments on the surface of a base material. Since a plurality of reactions can be conducted simultaneously, many types of reactive probes are used. The compartments for placing the tile-like carriers are preferably arranged in such a manner that the plurality of particulate or tile-like carriers loaded with the reactive probes can be arrayed by a mechanical or automatic procedure. The compartments are preferably formed in well-ordered array.

It further relates to a method for fabrication of a reactive probe chip, characterized in that after synthesizing oligonucleotides having desired base sequences on tile-like carriers, each tile-like carrier is immobilized in separate compartments on a base material. In this case, it is necessary to use means which can rapidly and sequentially convene the small tile-like carriers loaded with the oligonucleotides from contacting the surface in the compartments on the base material.

A composite substrate of still another aspect of the invention has a plurality of porous regions on at least a section of its surface, which regions are surrounded and comparted by non-porous regions.

Alternatively, the composite substrate has a plurality of non-porous regions which are surrounded and comparted by porous regions.

In the former case, for example, a specific catalytic reaction or enzyme reaction can take place only in the compartmented regions. Thus, if a sample is exposed to a substrate having a plurality of such regions comparted isolatedly each other, the sample will be allowed to simultaneous testing of the presence of reactivity for the plurality of reactions.

In the latter case, for example, a semiconductor fabrication process may be employed to partition a plurality of wirings (non-porous regions) by insulative porous regions and to form a highly insulated electrical wiring on the substrate.

The reactive substances or probes carried on the porous particles may be any of those which react with detection targets, for example, oligonucleotides, enzymes, antigens, antibodies, epitopes or proteins. A method wherein the reactive probes immobilized on each of the carriers are arrayed and set in the compartments on the base material surface can stably and flexibly produce the chips.

Two methods exist for loading the reactive substances on the inner pore surfaces of the porous carrier particles. One method is that oligonucleotides having desired base sequences or proteins with desired structures are synthesized on the porous carrier particles by a solid-phase method, to prepare the reactive substances in situ.

The other method is as follows. A purified extract from animal or plant cells or a synthesized reactive substance is bound by some method, for example, in the case of porous glass, reacting aminosilane with the porous glass surface to bind the amino groups. Using glutaraldehyde, various enzymes can be bond to the formed amino groups.

The reaction between the detection target and the reactive substances occurs in the pores of the porous carrier particles, and since the detection target must be incorporated in the pores of the porous carrier particles, the pores of the porous carrier particles must be large enough that the detection target can be moved into by the incorporated diffusion. The pore size usually ranges from 10 nm to 1 $\mu$m, and preferably 50 nm to 200 nm.

Reaction in the pores of the porous carrier particles can prevent side-reaction with contaminants, and the larger reactive surface area allows more accurate detection.

According to one aspect of the invention, highly stable, reactive substance-loaded porous carrier particles or tile-like plates can be stored because the reactive substance synthesized on the carrier is used as it is, or because the substances immobilized on the carriers in used in the detection.

While there are no particular restrictions on the method of arraying and immobilizing the reactive substance on the base material, a protective solution, such as a single amount of water may be contained in the carrier particles to protect the inner surface of the pores and then an inorganic base material such as silica sol is added to the carrier particles to make a slurry, which is arrayed on a support by use of a dispenser. This method is useful to fabricate a small number of reactive probe chips, but in order to mass-produce the reactive probe chips, the slurry may be used in the form of printing ink to form the array pattern by a multi-color printing method.

When using such methods, it will be difficult to form a slurry or ink if the size of the "loaded porous carrier particles" is very large, and therefore the porous carrier particle size preferably ranges from 1 $\mu$m to 100 $\mu$m, and more preferably from 3 $\mu$m to 20 $\mu$m. This is because a large particle size is preferred from the standpoint of handleability during the process of loading the reactive substance, but a small particle size is preferred when the porous carrier particles are immobilized after the reactive substances have been loaded; nevertheless, large grains may be used so long as they can be arrayed.

By using these methods it is possible to achieve stable and flexible production. The base material may be of a material which is stable and is not deteriorated upon using it in the detection system, but it must have surface properties suitable for immobilizing the porous carrier particles. Glass plates such as quartz glass, borosilicate glass and the like, or inorganic base materials such as silicon wafers are preferred.

Modification of the method of binding the porous carrier particles will enable to use of an organic base material such as a polyester film or polyethylene film, and in some cases even paper materials can be used. The base material surface may be appropriately treated for the purpose of adjusting the affinity with the carrier binding material.

The porous carrier particles must be of a material that can carry, as the reactive substances, any proteins having the desired structures or the oligonucleotides having the desired base sequences. The porous materials having a binding ability, such as porous glass, silica gel, ion-exchange resin and the like are preferred, among which porous glass is most preferred because its surface reactivity associated with pore sizes can be controlled.

The surface of the porous carrier particle is preferably subjected to appropriate surface treatment in order to adjust its affinity with the reactive substance or reactive probe.

There are no particular restrictions on the shape of the base material, and for example, it may be thin plate such as a film or sheet, or in a cubical, rod-like, cord-like or spherical shape.

When a thin plate is used, there are no particular restrictions on the thickness or size of the base material, and the thickness of the base material may be easily determined in consideration of the form stability required for the base material. The size of the base material may be easily determined on consideration of the number of microcompartments to be formed in the base material surface.

The microcompartments on the base material surface according to the invention are imaginary compartments, which are defined by imaginarily formed partitions and not materially separated.

The "reactivity" of the "reactive substances or reactive probes" according to the invention refers to not only a change in their chemical structure by ionic bonding or covalent bonding through a chemical reaction, but also the property capable of forming binding states with other substances due to Van der Waals forces, hydrogen bonding, coordination bonding, chemical adsorption, physical adsorption or the like.

Such reactive substances, which are alternatively referred to as reactive probes, include proteins with any desired structures and oligonucleotides with any desired base sequences, and naturally there are no restrictions on these.

There are no particular restrictions on the degree of integration of the microcompartments, i.e. the compartments for the reactive substances, in a reactive probe chip according to the invention. Since the degree of integration required or convenient will differ depending on the use of the reactive probe chip, the degree of integration may be appropriately changed to conform to the use.

As an example, there may be 100 or more microcompartments per $cm^2$ of the reactive probe chip surface, and if the base material and reactive substances are appropriately selected, about 10,000 microcompartments per $cm^2$ of surface can be formed.

Since the reactive probe chip of the invention has the reactive substances loaded on porous carrier particles, tiles or the like, the substance are not easily penetrated and released on the base material. Also, since the size of porous carrier particles is small, it is possible to immobilize a solution containing the particles at high density in the compartments on the base material.

The reactive substances carried on the porous carrier solid may be the same types of substances or different types of substances, depending on the use of the reactive probe chip. From the viewpoint of working efficiency, it is preferred to load a plurality of reactive substances at one time, and it is more preferred to load all of the reactive substances at one time.

The reactive substance-loaded porous carrier solid may be separately prepared and stored, or if necessary, they may be immobilized on the base material in the necessary combinations. Especially, it is practical in the case of oligonucleotide-synthesized porous carrier particles or tiles, because a usual synthesis process can be used.

The size and shape of the carriers may be selected as desired, but considering immobilization of the carriers loaded with a plurality of different reactive probes onto the substrate, when tile-like carrier is used, it is preferably a plate with a square shape having a size of from 50 $\mu$m to 5 mm on each side, or a hexagonal or circular shape, and squares of 100 $\mu$m to 1 mm are particularly preferred. The thickness will depend on the size, but it is preferably in the range of 100–200 $\mu$m. The immobilization of the tile-like carriers on the base material may be mechanically attached and immobilized on the substrate using an adhesive which does not affect the reaction.

For example, an acrylic resin may be used as an adhesive for immobilization of the tile-like carriers onto the substrate.

The apparatus used for immobilization of the tile-like carriers onto the substrate may be one used for processing and conveyance of micromembers used in the production of semiconductor devices.

In case the tile-like carrier is used, a process for fabrication of a reaction chip according to the invention will now be explained with reference to the attached drawings.

Figure 5:
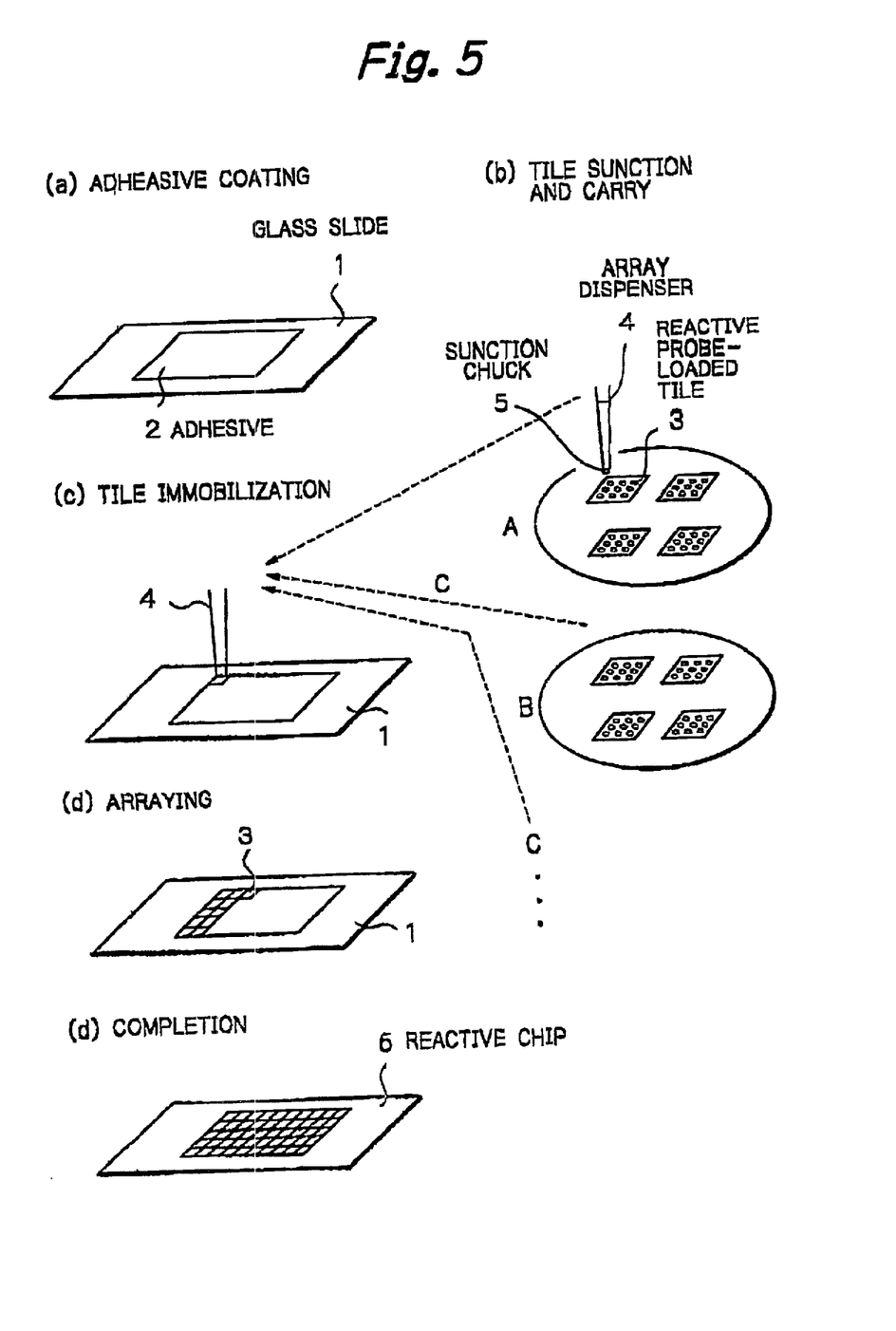
FIG. 5 is an illustration of a fabrication process for a reactive probe chip according to the invention.

FIG. 5 is an illustration of the fabrication process, and in step (a), an adhesive 2 is coated on the area in which the reactive probes are to be set on the glass slide 1 serving as the base material for the reaction chip.

In step (b), an array dispenser 4 with a suction chuck 5 at the lower end is moved to Region A which contains base materials bearing a plurality of the same reactive probe-loaded tiles 3 manufactured in advance, and a reactive probe-loaded tile 3 is suctioned with the suction chuck 5, and then in step (c), the array dispenser 4 is moved over the glass slide 1, disengaging the suction for ejection at the prescribed location, and immobilizing the reactive probe-loaded tile 3 it has carried onto the prescribed location.

Then, in step (d), a tile 3 is conveyed by the array dispenser 4 from Region B which contains substrates bearing a different plurality of reactive probe-loaded tiles 3 and is immobilized at the subsequent prescribed location, and this operation is repeated in order to arrange different types of reactive probe-loaded tiles 3.

This yields, in step (e), a reaction chip 6 with different types of reactive probe-loaded tiles 3 orderly arranged at prescribed locations.

The porous solid for producing a composite substrate of the still another aspect of the invention is preferably porous glass or porous ceramic which enables to easily control the pore size and to easily attache functional groups thereto. Split-phase porous glass with a high density of surface hydroxyl groups, which readily undergoes chemical modification, is especially suitable for use as a reaction site.

The sample can also be rendered homogeneous by flattening the surface by a process such as polishing.

The split-phase porous glass has properties which allow easy control of the pore size by appropriately selecting the heat treatment time and temperature, and borosilicate glass is preferred as the parent glass composition.

Porous glass compositions include $Na_2O$—$B_2O_3$—$SiO_2$ based glass with $SiO_2$ in a range of 55–80 wt % or $SiO_2$ in a range of 35–55 wt %, as well as $SiO_2$—$B_2O_3$—$CaO$—$Al_2O_3$ based glass, $SiO_2$—$P_2O_5$—$Na_2O$ based glass, $SiO_2$—$B_2O_3$—$CaO$—$MgO$—$Al_2O_3$—$TiO_2$ based glass, $SiO_2$—$B_2O_3$—$Na_2O$—$GeO_2$ based glass, $SiO_2$—$ZrO_2$ based glass and $GeO_2$—$ZrO_2$—$ThO_2$ based glass.

As porous ceramics there may be mentioned alumina, magnesia and the like.

Several differing methods may be used as fabrication methods for the composite substrate of the invention.

One is a method whereby a separately formed porous solid is situated on prescribed regions of a non-porous substrate. The porous solid used here may be particulate, or crushed or cut fragments of a porous solid plate. The porous solid may also be given a necessary function, for example, by loading a reactive probe or reactive substance on the porous solid, prior to being arrayed on the substrate.

For arraying on the substrate, it is preferred to use an adhesive that does not affect the function of the reactive probes or the porous solid, such as water glass. Pits may also be preformed in the base material and the porous solid embedded therein, and then the entire substrate subjected to polishing to create a flat composite substrate.

Another method is one whereby a plurality of porous solid precursors (substances) are situated on prescribed regions of a non-porous substrate and pores are produced therein on the base material. The method of situating the precursors may be a method of attachment of solids with an adhesive or the like, or a method of dropping a liquid or slurry and heat treating it to form a precursor (for example a precursor substance layer) attached to the substrate.

In this case as well, pits may be preformed at prescribed locations in the substrate and the porous solid precursors embedded therein, and polishing carried out after production of the pores to obtain a flat composite substrate.

Another possible method involves preparing a substrate composed of a porous solid precursor, or forming a porous solid precursor layer or thin-film over the entirety of a non-porous substrate, and producing pores in prescribed regions thereof.

The method of forming the precursor on the non-porous substrate may be a method of attachment of a plate with an adhesive, uniform coating of a solution or slurry by pin coating or the like, or attachment on the substrate by heat treatment or the like. For production of the pores, a resist may be used to cover the other sections in order to produce pores only in the prescribed locations. In this case, the surface of the substrate is relatively flat prior to pore production, but if necessary it may be further flattened by polishing.

By preparing a substrate which is porous over the entirety and eliminating the pores in prescribed regions of the surface by sealing treatment, with the prescribed regions selected at locations that form the borders for the porous sections so that they are separated by a plurality of compartments, it is possible to form a surface with a plurality of porous regions compartmented by non-porous formed regions.

The sealing method used to accomplish this may be a method of irradiation of the prescribed regions with a high energy beam such as a laser beam, or a method of chemical treatment after coating the regions to be left porous with a resist. Laser processing is preferred because only the regions exposed to the laser are melted, and there is less effect on the other locations. Laser processing can also easily form a plurality of compartmented regions by simply shifting the laser at spacings on the substrate to draw horizontal and vertical lines.

EXAMPLES

The present invention will be illustrated in detail by way of examples. It is to be understood, however, that the invention is in no way limited by these examples.

Example 1

Proteins with different structures were synthesized on particles of a surface-aminated ion-exchange resin powder having a mean particle size of 10 $\mu$m and an average pore size of 10 nm.

Figure 1:
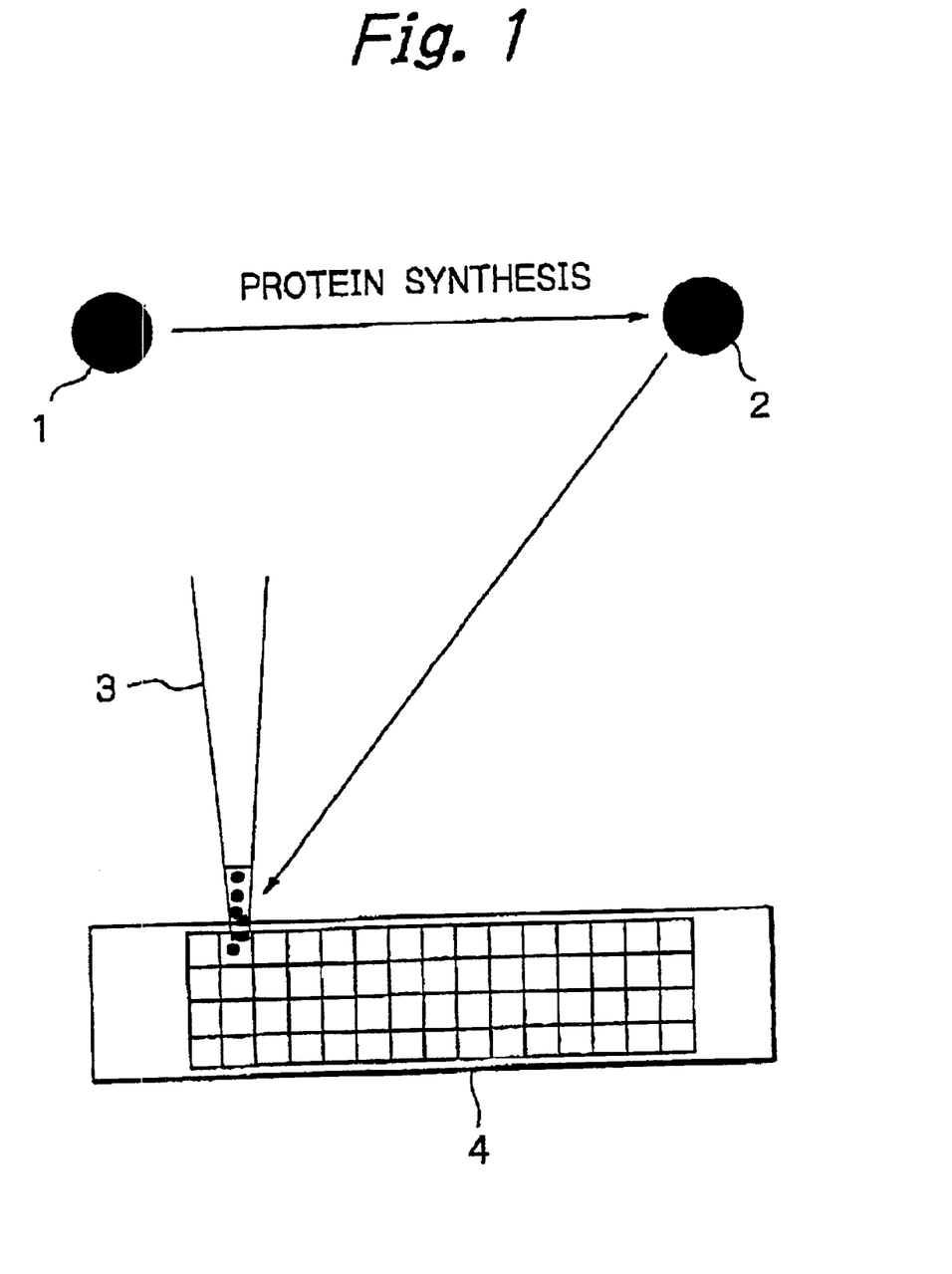
FIG. 1 is an illustration showing a process for fabrication of a reactive probe chip using a carrier particle immobilizing apparatus according to Example 1.

The protein-loaded porous ion-exchange resin powder was dispersed In purified water and silica sol was added to prepare a slurry. The slurry was then loaded in each of 1 mm-square compartments of the surface of a glass plate 4 composed of a borosilicate glass slide (approximately 15 cm×2 cm), using the ultrathin capillary of the carrier particle binding apparatus (dispenser) 3 shown in FIG. 1. A reactive probe chip capable of carrying out reactions with 750 different proteins was thus fabricated.

Example 2

Different oligonucleotides were synthesized by an established method on aminosilylated silica gel particles 5 for liquid chromatography having a diameter of 3 nm and a pore size of 10 nm.

Figure 2:
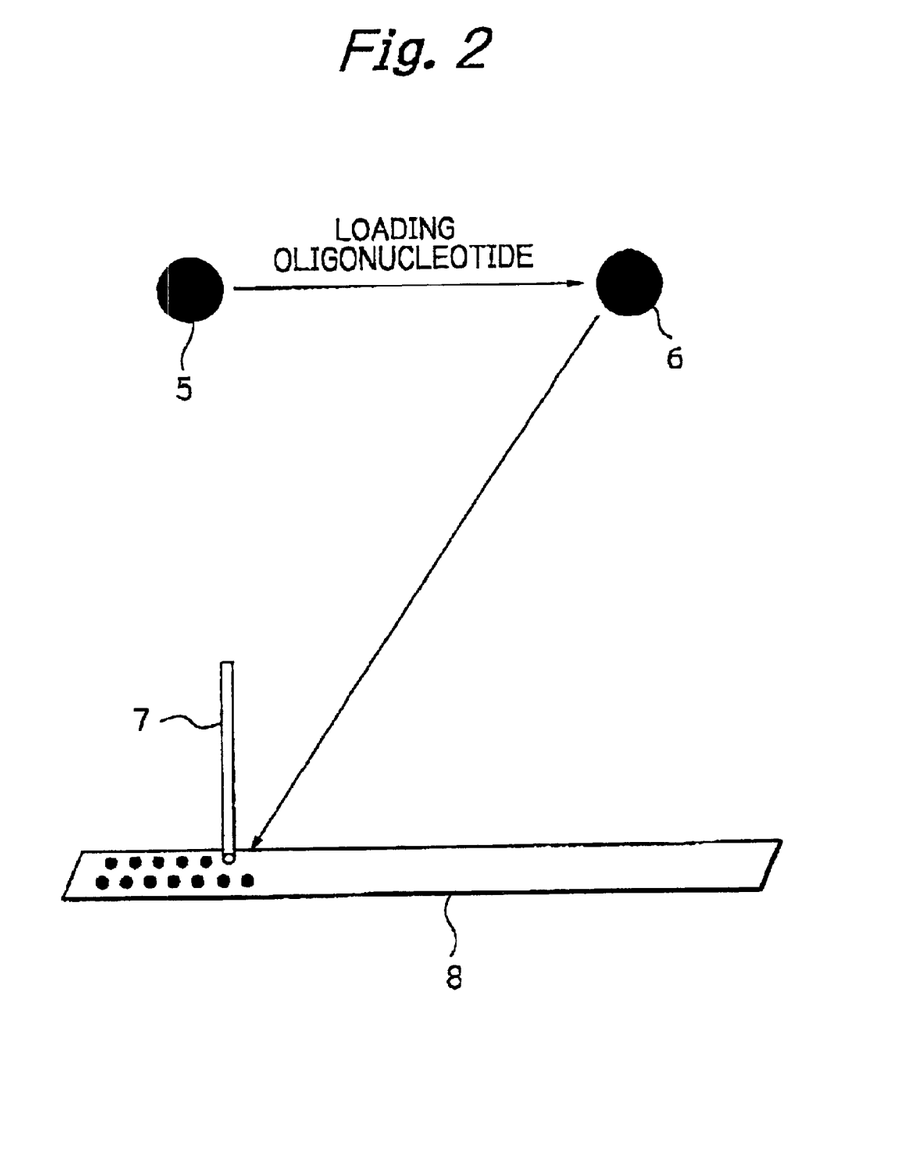
FIG. 2 is an illustration showing a process for fabrication of a reactive probe chip using a carrier particle immobilizing pin according to Example 2.

A slurry prepared by adding an aqueous polyvinyl alcohol solution to this oligonucleotide-immobilized silica gel was held onto the carrier particle-immobilizing pin 7 shown in FIG. 2, and then immobilized at a pitch 0.5 mm on the surface of a ribbon-shaped silica gel coated polyester film 8 having a size of approximately 0.5 cm×20 cm, to obtain a reactive probe chip according to the invention.

Example 3

Porous glass powder with a pore size of 50 nm and a diameter of 5 $\mu$m with a γ-aminopropylsilylated surface was used to synthesize different oligonucleotides by an established method.

Figure 3:
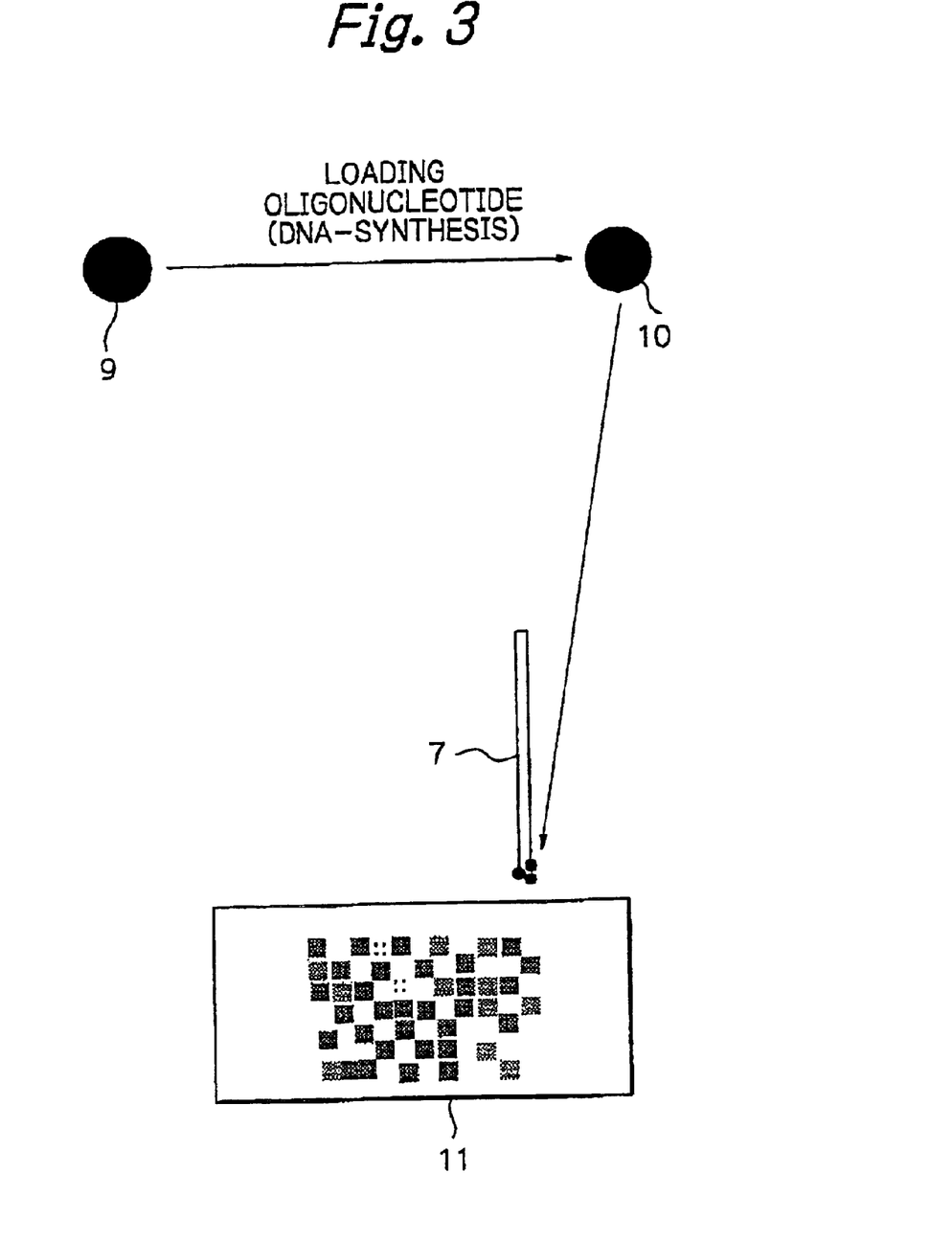
FIG. 3 is an illustration showing a process for fabrication of a reactive probe chip using a carrier particle immobilizing pin according to Example 3.

A slurry prepared by adding an acryl polymer to the oligonucleotide-loaded porous glass powder was held on the carrier particle-immobilizing pin 7 shown in FIG. 3, and then arrayed and immobilized at a pitch of 0.5 mm on the surface of an oxide film-coated silicon chip 11 having a size of approximately 1 cm×1 cm, to obtain a reactive probe chip according to the invention.

Example 4

Porous glass powder with a pore size of 100 nm and a diameter of 5 $\mu$m with a γ-aminopropylsilylated surface was used to synthesize different oligonucleotides by an established method.

Figure 4:
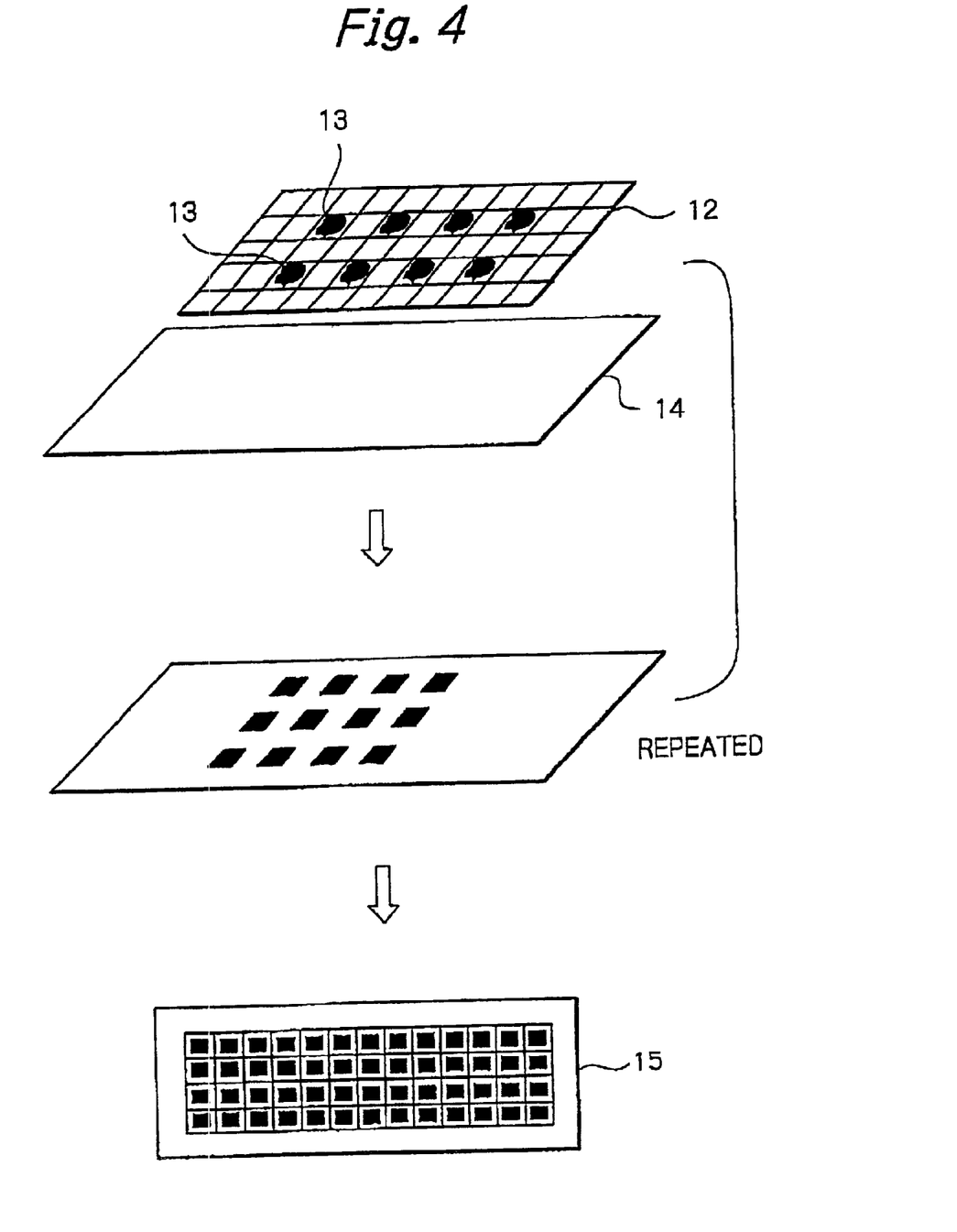
FIG. 4 is an illustration showing a process for fabrication of a reactive probe chip by screen printing according to Example 4.

An acryl polymer was added to each of the porous glass powders loaded with different oligonucleotides, to prepare pastes containing porous glass powders loaded with the different oligonucleotides. The pastes 13 were immobilized at a pitch of 0.5 mm on the surface of a slide glass 14 (approximately 1 cm×1 cm), which had been subjected to a surface blasting treatment to make the surface delustered. The immobilization was carried out by using a multicolor screen printing technique, and this printing was repeated (1–n) times to obtain a reactive probe chip 15 according to the invention.

Example 5

An enzyme with a certain specific reactivity was immobilized on a 1 mm-square, 10 μm-thick surface aminated "cover glass" using glutaraldehyde. A "cover glass" loaded with different enzymes was also prepared in the same manner, and these were consecutively arranged on an acrylic adhesive-coated glass slide having a length of 75 mm, a width of 25 mm and a thickness of 1.5 mm, using an aligning apparatus which was a modified semiconductor wire bonder. These were loaded into each of several 1 mm-square compartments. A reactive probe chip capable of carrying out 100 different antigen enzyme reactions was thus fabricated.

Example 6

Different oligonucleotides were synthesized by an established method on surface-aminated porous glass with a size of 0.5 mm square and a thickness of 10 μm. The oligonucleotide-immobilized porous glass was orderly arranged on an acrylic adhesive-coated glass slide with dimensions of 75 mm length, 25 mm width and 1.5 mm thickness. A 1000-type complementary DNA detection chip was fabricated.

Example 7

Different oligonucleotides were synthesized by an established method on surface-aminated porous glass with a size of 0.5 mm square and a thickness of 10 μm. The oligonucleotide-immobilized porous glass was orderly arranged on the surface of an epoxy adhesive-coated polyester film (approximately 3 cm×20 cm, 0.3 mm thickness) at a 0.5 mm pitch, to obtain a reactive probe chip according to the invention.

Example 8

Figure 6:
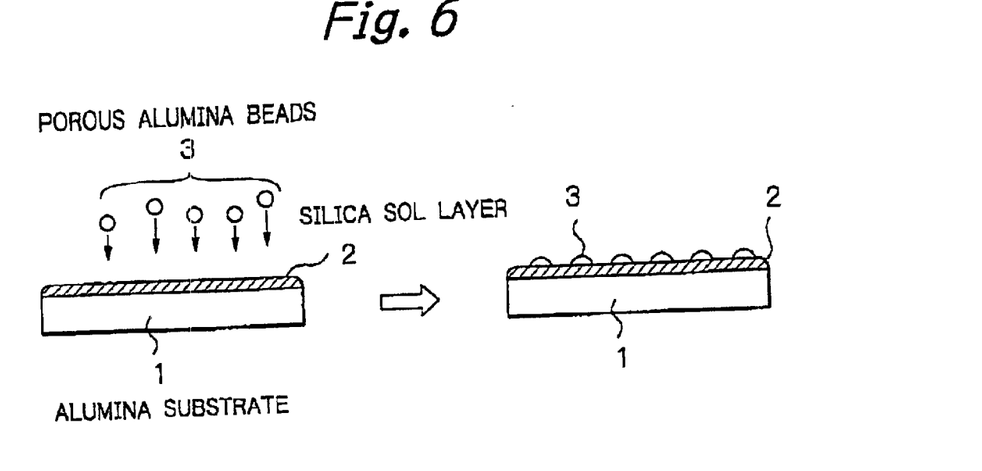
FIG. 6 is an illustration of a fabrication process for an alumina substrate having a plurality of porous alumina bead regions on the surface.

As shown in FIG. 6, an alumina substrate 1 with dimensions of 100 mm length×100 mm width×1 mm thickness was coated with silica sol to form a silica sol layer 2, and then porous alumina beads 3 with a mean particle size of 50 μm were dispersed thereover and dried for immobilization.

The porous alumina beads 3 had a void volume of 40% and a surface area to weight ratio of 250 $m^2/g$, and the individual particles can carry agents with different functions.

Example 9

Figure 7:
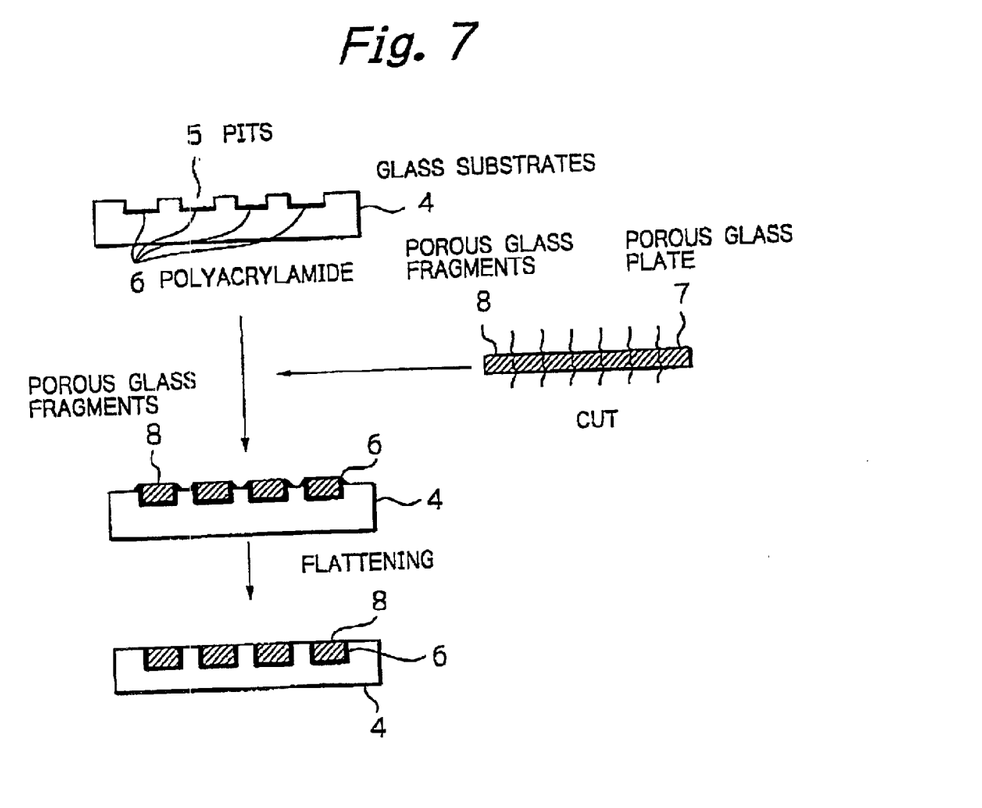
FIG. 7 is an illustration of a fabrication process for a glass plate having a plurality of porous glass regions on the surface.

As shown in FIG. 7, a plurality of pits 5 with dimensions of 3 mm length×3 mm width and 0.1 mm depth were formed by wet etching on prescribed locations of the surface of a glass plate 4 with dimensions of 75 mm length, 25 mm width×1.5 mm thickness. Polyacrylamide 6 was placed in the pits 5.

A 0.2 mm-thick porous glass plate 7 was cut into sizes insertable in the pits 5, and the porous glass fragments 8 were placed on the polyacrylamide 6 in the pits 5, and attached therein. This caused a portion of the polyacrylamide 6 to spill over the edges of the pits 5, or else the tops of the porous glass fragments 8 protruded above the surface of the glass plate 4. The attached substrate is subjected to flattening treatment if necessary.

This method yielded a glass plate 4 having polyacrylamide 6 in a plurality of pits 5, with porous glass fragments 8 immobilized by the polyacrylamide 6.

By dropping a function-providing reagent onto the porous glass fragment 8 sections using a micropipette, it is possible to manufacture a functional glass plate.

If the properties of the functional substances carried on the porous glass fragments 8 are such that the functional substances are affected by the polyacrylamide, the polyacrylamide may be changed to another adhesive polymer.

Example 10

Figure 8:
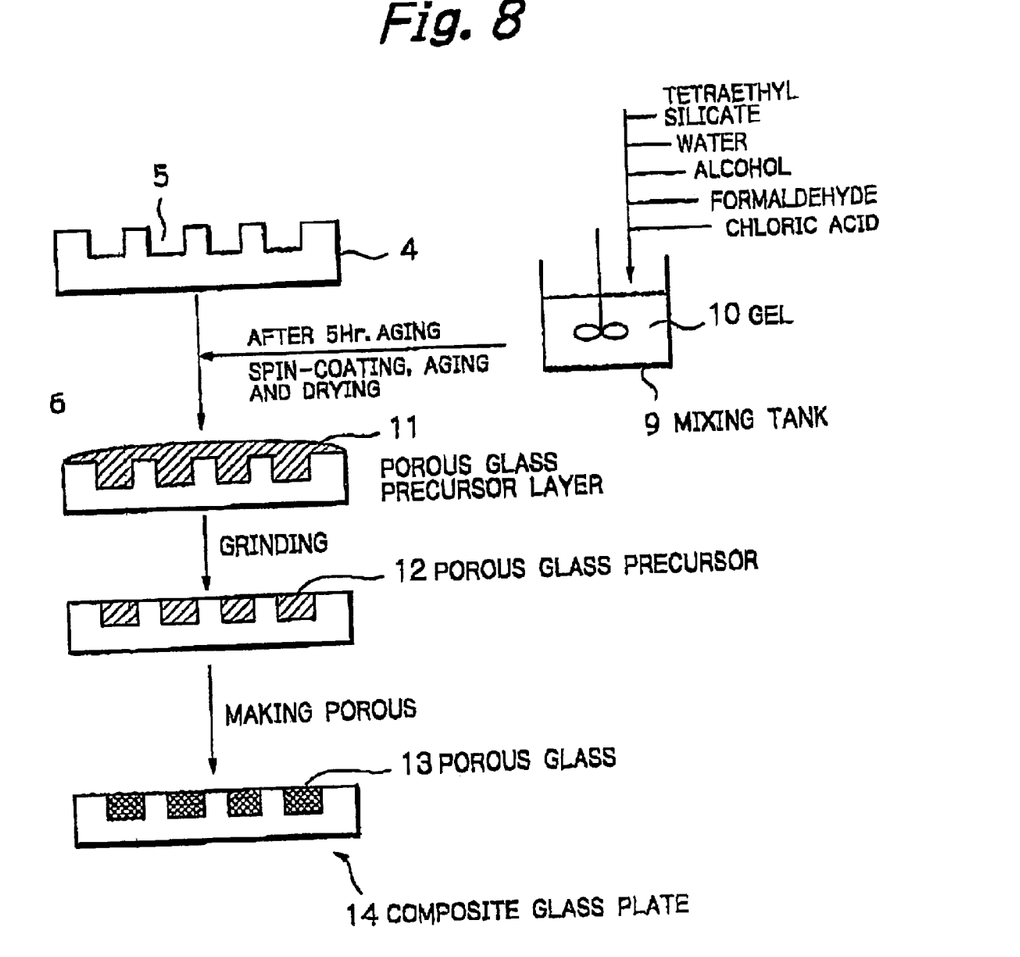
FIG. 8 is an illustration of a process for fabrication of a glass plate having a plurality of porous glass regions by coating of a porous glass precursor on the surface.

As shown in FIG. 8, a plurality of pits 5 with dimensions of 3 mm length×3 mm width and 0.2 mm depth were formed by wet etching on prescribed locations of the surface of a glass plate 4 with dimensions of 75 mm length, 25 mm width×1.5 mm thickness.

After adding 2 ml of water, 4 ml of formamide and 0.2 ml of 12 N hydrochloric acid to a solution of 2 ml tetraethyl silicate in 2 ml of ethyl alcohol in a separate stirring tank, for hydrolysis of the tetraethyl silicate, it was aged for 5 hours at room temperature and then a highly viscous gel 10 of a porous glass precursor was formed.

This was spin coated onto the surface of a glass plate 4 (to 0.3 mm thickness), aged and dried, to form a porous glass precursor layer 11. Next, the porous glass precursor layer 11 sections were polished to remove the sections raised from the surface of the glass plate 4, to give a glass plate having a porous glass precursor 12 only on the sections of the pits 5.

Finally, the porous glass precursor 12 was treated to convert it to porous glass 13, to give a composite glass plate 14 having a plurality of porous glass regions in non-porous glass regions.

Example 11

Figure 9:
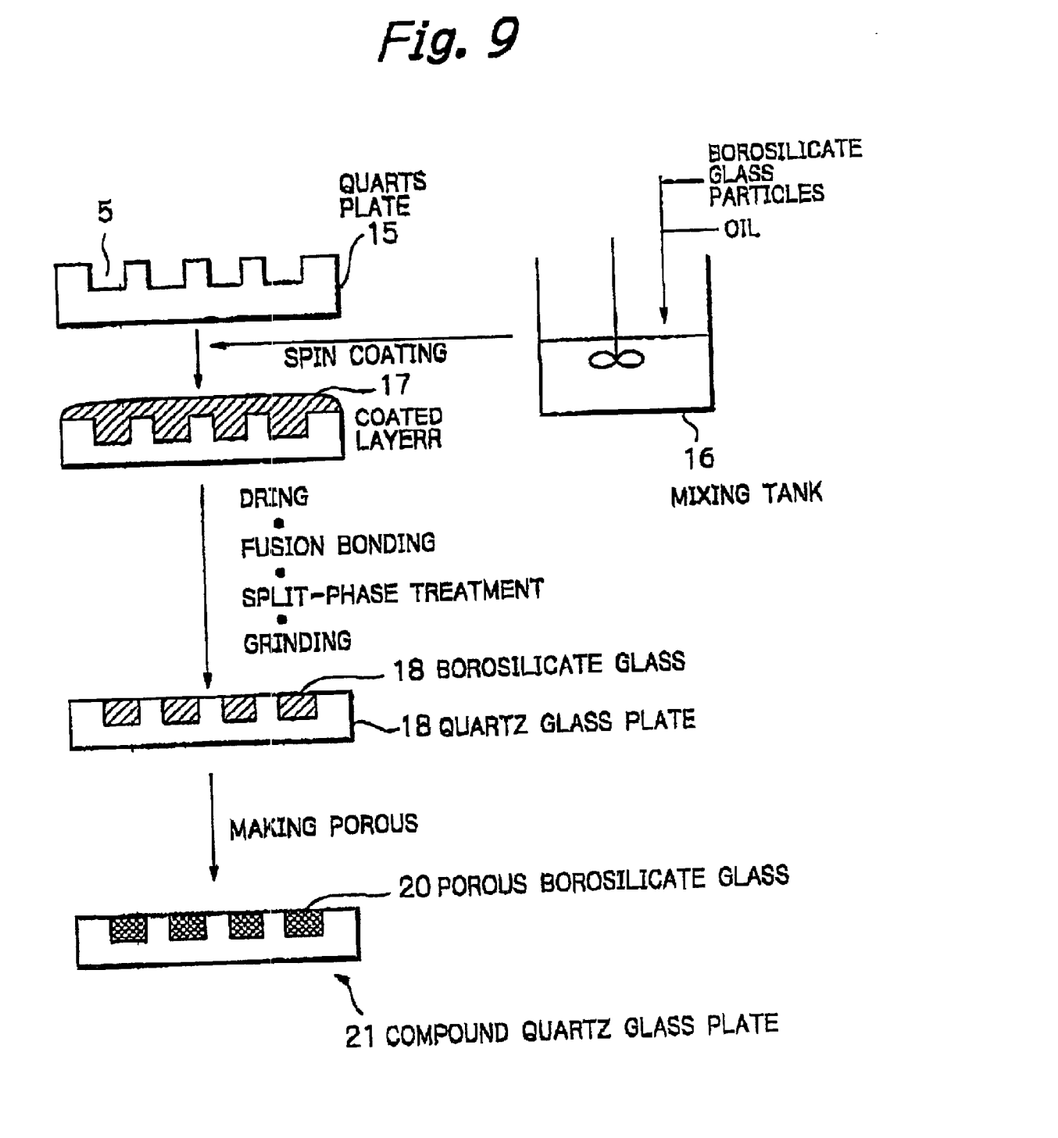
FIG. 9 is an illustration of a process for fabrication of a quartz plate having a plurality of porous glass regions by a split-phase method with coating of borosilicate glass particles on the surface.

As shown in FIG. 9, a plurality of pits 5 with dimensions of 3 mm length×3 mm width and 0.15 mm depth were formed by cutting on prescribed locations of the surface of a quartz plate 15 with dimensions of 75 mm length, 30 mm width×1.5 mm thickness.

Borosilicate glass particles with a mean particle size of 10 μm and an oil (paraffin wax) were placed in an stirring tank 16 and stirred to form a coating solution, which was then coated onto the surface of the quartz plate 15 by screen printing to form a coating layer 17. The coating coverage was 400 $g/m^2$.

This was dried and heat treated to remove the oil portion, subsequently heated at 850° C. for 30 minutes to fused together the borosilicate glass particles, and then heat treated at 600° C. for 15 hours for split-phase treatment. The borosilicate glass sections 18 were then polished to remove the sections raised above the surface of the glass plate 10, to give a quartz glass plate 19 having borosilicate glass 18 only in the sections of the pits 5.

This quartz glass plate 19 was acid treated for 0.5 hour using sulfuric acid (1 N concentration) at approximately 90° C. to produce pores, thus giving a composite quartz glass plate 21 having a plurality of porous borosilicate glass regions 20.

According to the invention, it is possible to easily and cheaply provide a reactive probe chip having reactive probes such as DNA fragments integrated on its surface, without the need for special equipment such as photolithography equipment. Also, selection of the base material and modifications to the method of loading the reactive probes can provide a chip with a higher degree of integration than existing DNA chips.

By preparing a carrier loaded with different reactive probes, it is possible to more conveniently supply chips loaded with the necessary combinations of DNA probes for necessary occasions, while also allowing construction of a reactive probe chip with different types of reactive probes immobilized and thereby providing a DNA chip of lower cost and higher stability that can be helpful in the clinic for detection of individual DNA polymorphisms.

According to another aspect of the invention there is provided a composite substrate wherein a plurality of porous regions are orderly arranged as compartments on at least a section of the surface thereof, and therefore a plurality of different functions or performances can be exhibited on the same substrate, thus offering applicability not found in the prior art.

For fabrication of the composite substrate, porous glass fragments are immobilized onto the substrate at a prescribed spacing via an adhesive layer, or anchorable sites such as pits are formed in the substrate at a prescribed spacing and the porous glass fragments are immobilized therein, as a simple means of orderly arranging a plurality of porous regions in compartments.

What is claimed is:

1. A reactive probe chip for detecting target functional molecules, comprising:
   one or a plurality of first carrier probes, wherein said first carrier probe is a porous carrier in the form of a particle, having immobilized within the pores thereof a first reactive substance capable of bonding a first target molecule;
   one or a plurality of second carrier probes, wherein said second carrier probe is a porous carrier in the form of a particle, having immobilized within the pores thereof a second reactive substance capable of bonding a second target molecule; and
   a substrate material,
   wherein said one or a plurality of first carrier probes and said one or a plurality of second carrier probes are immobilized on a surface of said substrate material, with the proviso that the porous carrier of said first and second carrier probes is other than silica gel.

2. A reactive probe chip in accordance with claim 1, wherein said first and second reactive substances are selected from the group consisting of oligonucleotides, enzymes, antigens, antibodies, epitopes or proteins.

3. A reactive probe chip in accordance with claim 2, wherein said first and second reactive substances are oligonucleotides.

4. A reactive probe chip in accordance with claim 3, wherein said oligonucleotides are synthesized directly on said porous carrier.

5. A reactive probe chip in accordance with claim 1, wherein said porous carrier has a pore size within the range of 10 nm to 1 $\mu$m.

6. A reactive probe chip in accordance with claim 5, wherein said pore size is a minimum of 50 nm.

7. A reactive probe chip in accordance with claim 1, wherein said first and second carrier probes are immobilized on the surface of the said substrate material by means of an adhesive.

8. A reactive probe chip in accordance with claim 1, wherein said porous carrier is a porous glass or ion-exchange resin.

9. A reactive probe chip in accordance with claim 8, wherein said porous carrier is a porous glass.

10. A reactive probe chip in accordance with claim 1, wherein said substrate material is an inorganic or organic substrate.

11. A reactive probe chip in accordance with claim 1, wherein said porous carrier particles have a particle size of 1 $\mu$m to 100 $\mu$m.

12. A reactive probe chip in accordance with claim 11, wherein said porous carrier particles have a particle size of 3 $\mu$m to 20 $\mu$m.

13. A reactive probe chip in accordance with claim 1, wherein a plurality of said first carrier particle probes and a plurality of second carrier particle probes are immobilized on said substrate material surface, each in a discrete microcompartment.

14. A reactive probe chip in accordance with claim 13, wherein a plurality of additional carrier particle probes, each carrying a different additional reactive substance immobilized thereon, is also immobilized on the surface of said substrate material, each in its own discrete microcompartment.

15. A reactive probe chip in accordance with claim 14, wherein said discrete microcompartments are arranged in an array.

16. A reactive probe chip in accordance with claim 15, wherein said array has 100 to about 10,000 microcompartments per $cm^2$ of surface.

17. A method for fabrication of a reactive probe chip in accordance with claim 1, comprising:
   immobilizing said first and second reactive substances within the pores of said first and second porous carriers to form first and second loaded carriers; and
   immobilizing said first and second loaded carriers on a surface of said substrate material.

18. A method in accordance with claim 17, wherein said first and second reactive substances are selected from the group consisting of oligonucleotides, enzyme, antigens, antibodies, epitopes or proteins.

19. A method in accordance with claim 18, wherein said first and second reactive substances are oligonucleotides.

20. A method in accordance with claim 19, wherein said oligonucleotides are immobilized on said porous carriers by synthesizing said oligonucleotides directly on said porous carriers.

21. A method in accordance with claim 17, wherein said porous carrier has a pore size within the range of 10 nm to 1 $\mu$m.

22. A method in accordance with claim 19, wherein said pore size is a minimum of 50 nm.

23. A method in accordance with claim 17, wherein said step of immobilizing said first and second loaded carriers on a surface of said substrate material comprises immobilizing said loaded carriers on the surface of said substrate material by means of an adhesive.

24. A method in accordance with claim 17, wherein said porous carrier is a porous glass or ion-exchange resin.

25. A method in accordance with claim 24, wherein said porous carrier is a porous glass.

26. A method in accordance with claim 17, wherein said substrate material is an inorganic or organic substrate.

27. A method in accordance with claim 17, wherein said porous carrier particles have a particle size of 1 $\mu$m to 100 $\mu$m.

28. A method in accordance with claim 27, wherein said porous carrier particles have a particle size of 3 μm to 20 μm.

29. A method in accordance with claim 17, wherein a plurality of said first carrier particle probes and a plurality of second carrier probes are immobilized on said substrate material surface, each in a discrete microcompartment.

30. A method in accordance with claim 29, wherein a plurality of additional carrier particle probes, each carrying a different additional reactive substance immobilized thereon is also immobilized on the surface.

31. A method in accordance with claim 30, wherein said discrete microcompartments are arranged in an array.

32. A method in accordance with claim 31, wherein said array has 100 to about 10,000 microcompartments per $cm^2$ of surface.

33. A DNA chip for detecting target DNA, comprising:
one or a plurality of first carrier probes, wherein said first carrier probe is a porous carrier in the form of a particle, having immobilized within the pores thereof a first reactive substance capable of bonding a first target DNA;
one or a plurality of second carrier probes, wherein said second carrier probe is a porous carrier in the form of a particle, having immobilized within the pores thereof a second reactive substance capable of bonding a second target DNA; and
a substrate material,
wherein said one or a plurality of first carrier probes and said one or a plurality of second carrier probes are placed on a surface of said substrate material, with the proviso that the porous carrier of said first and second carrier probes is other than silica gel.

34. A DNA chip in accordance with claim 33, wherein said first and second reactive substances are oligonucleotides.

35. A DNA chip in accordance with claim 34, wherein said oligonucleotides are synthesized directly on said porous carrier.

36. A DNA chip in accordance with claim 33, wherein said porous carrier has a pore size within the range of 10 nm to 1 μm.

37. A DNA chip in accordance with claim 36, wherein said pore size is a minimum of 50 nm.

38. A DNA chip in accordance with claim 33, wherein said first and second carrier probes are immobilized on the surface of the said substrate material by means of an adhesive.

39. A DNA chip in accordance with claim 33, wherein said porous carrier is a porous glass or ion-exchange resin.

40. A DNA chip in accordance with claim 39, wherein said porous carrier is a porous glass.

41. A DNA chip in accordance with claim 33, wherein said substrate material is an inorganic or organic substrate.

42. A DNA chip in accordance with claim 33, wherein said porous carrier particles have a particle size of 1 μm to 100 μm.

43. A DNA chip in accordance with claim 42, wherein said porous carrier particles have a particle size of 3 μm to 20 μm.

44. A DNA chip in accordance with claim 33, wherein a plurality of said first carrier particle probes and a plurality of second carrier particle probes are placed on said substrate material surface, each in a discrete microcompartment.

45. A DNA chip in accordance with claim 44, wherein a plurality of additional carrier particle probes, each carrying a different additional reactive substance immobilized thereon, is also placed on the surface of said substrate material, each in its own discrete microcompartment.

46. A DNA chip in accordance with claim 45, wherein said discrete microcompartments are arranged in an array.

47. A DNA chip in accordance with claim 46, wherein said array has 100 to about 10,000 microcompartments per $cm^2$ of surface.

48. A method for fabrication of a DNA chip in accordance with claim 33, comprising:
immobilizing said first and second reactive substances within the pores of said first and second porous carriers to form first and second leaded carriers; and
placing said first and second loaded carriers on a surface of said substrate material.

49. A method in accordance with claim 48, wherein said first and second reactive substances are oligonucleotides.

50. A method in accordance with claim 49, wherein said oligonucleotides are immobilized on said porous carriers by synthesizing said oligonucleotides directly on said porous carriers.

51. A method in accordance with claim 48, wherein said porous carrier has a pore size within the range of 10 nm to 1 μm.

52. A method in accordance with claim 49, wherein said pore size is a minimum of 50 nm.

53. A method in accordance with claim 48, wherein said step of placing said first and second loaded carriers on a surface of said substrate material comprises immobilizing said loaded carriers on the surface of said substrate material by means of an adhesive.

54. A method in accordance with claim 48, wherein said porous carrier is a porous glass or ion-exchange resin.

55. A method in accordance with claim 54, wherein said porous carrier is a porous glass.

56. A method in accordance with claim 48, wherein said substrate material is an inorganic or organic substrate.

57. A method in accordance with claim 48, wherein amid porous carrier particles have a particle size of 1 μm to 100 μm.

58. A method in accordance with claim 57, wherein said porous carrier particles have a particle size of 3 μm to 20 μm.

59. A method in accordance with claim 48, wherein a plurality of said first carrier particle probes and a plurality of second carrier probes are placed on said substrate material surface, each in a discrete microcompartment.

60. A method in accordance with claim 59, wherein a plurality of additional carrier particle probes, each carrying a different additional reactive substance immobilized thereon is also placed on the surface.

61. A method in accordance with claim 60, wherein said discrete microcompartments are arranged in an array.

62. A method in accordance with claim 61 wherein said array has 100 to about 10,000 microcompartments per $cm^2$ of surface.

* * * * *